United States Patent [19]

Ingram

[11] Patent Number: 5,286,388
[45] Date of Patent: Feb. 15, 1994

[54] METHOD FOR NEUTRALIZING HEPARIN IN WHOLE BLOOD TAKEN FROM AN EXTRACORPOREAL CIRCUIT

[76] Inventor: John M. Ingram, 14120 Harpers Ferry St., Davie, Fla. 33325

[21] Appl. No.: 718,279

[22] Filed: Jun. 20, 1991

[51] Int. Cl.⁵ .............................................. B01D 61/00
[52] U.S. Cl. ..................... 210/650; 210/749; 210/765; 436/177; 436/178; 604/4; 604/5
[58] Field of Search ............... 210/638, 639, 646, 647, 210/650, 749, 765, 767; 604/4, 5, 7, 403, 408, 409; 435/2; 436/177, 178; 356/39

[56] References Cited

U.S. PATENT DOCUMENTS

| | | | |
|---|---|---|---|
| 4,199,502 | 4/1980 | Babson et al. | 210/690 |
| 4,209,392 | 6/1980 | Wallace | 210/646 |
| 4,322,298 | 3/1982 | Persidsky | 210/787 |
| 4,500,309 | 2/1985 | Diederich et al. | 210/646 |
| 4,800,016 | 1/1989 | Yang | 210/502.1 |
| 4,911,549 | 3/1990 | Karkar | 128/633 |
| 4,935,204 | 6/1990 | Seidel et al. | 210/646 |
| 4,938,873 | 7/1990 | Rossi | 210/647 |

*Primary Examiner*—Robert A. Dawson
*Assistant Examiner*—Sun Uk Kim
*Attorney, Agent, or Firm*—Malin, Haley, DiMaggio & Crosby

[57] ABSTRACT

A method for heparin neutralization within a blood bag containing whole blood and CPDA anti-coagulant, or the like, recovered from an extracorporeal circuit having heparin induced into the blood for reuse in a patient without further treatment thereof, by use of commercially available components wherein a modified blood bag containing CPDA and whole blood is infused with a calculable amount of protamine.

24 Claims, 2 Drawing Sheets

METHOD FOR NEUTRALIZING HEPARIN IN WHOLE BLOOD TAKEN FROM AN EXTRACORPOREAL CIRCUIT

FIELD OF THE INVENTION

This invention relates generally to the removal of heparin in an extracorporeal circuit and, more particularly, to a method of heparin neutralization within a blood bag containing whole blood and CPDA anticoagulant, or the like, for reuse in a patient without further treatment thereof.

BACKGROUND OF THE INVENTION

Blood is composed of a variety of elements. Approximately 45% of blood volume is composed of red cells (erythrocytes), white cells (leukocytes) and platelets. The acellular element of plasma makes up the remaining portion of blood of which approximately 90% is water. The remaining portion comprises proteins, antibodies, antigens, imune complexes, pathogens, toxins and other various organic and inorganic matter.

During surgical operations an extracorporeal circuit is frequently employed for a variety of purposes such as in the use of a heart-lunq machine. The blood is delivered to the circuit outside the body, or "extracorporeally." Such a circuit allows the surgeon to provide life sustaining treatment through the blood while performing surgery. As it is known, a large amount of fluid is needed to prime and operate such a circuit, said fluid comprising the patient blood as well as additional water to make up for volume of the circuit flow passageways.

During certain surgical procedures an anti-coagulant such as heparin is introduced into the extracorporeal circuit to prevent the blood from clotting while it is outside the patient. The situation then arises where the plasma is "contaminated" by the heparin, for it cannot be infused into the patient as large dosages of heparin will prevent the patient's blood from its natural coagulation by impeding the patients blood from performing its natural clotting ability. For this reason the red blood cells (erythrocytes) are separated from the plasma, and the whole blood re-infused into the patient, allowing the patient to maintain a portion of his own cellular blood components while the plasma is discarded. Commensurate with the loss of plasma is the loss of blood proteins having the highly desired clotting factors.

The major disadvantage of this procedure is that the loss of plasma reduces the patients' ability to heal or result in hemorrhaging, especially in a patient who has completed cardiopulmonary bypass. This most critical of patients is infused under current procedure, with only a portion of his own whole blood because the remaining blood volume, which was once the patient's own plasma, is lost.

Further aggravating the situation, donor plasma may be needed to increase a patient's blood volume, which comes from unknown, and possibly undesirable, donors. Problems include the need to screen donor plasma for pathogens such as the immune deficiency virus ("HIV") which can cause the acquired immune deficiency syndrome ("AIDS"). Further, problems can exist in depleting the patient's body of a naturally developed balance of blood that cannot be duplicated in a laboratory. This balance can speed the recovery process of the patient and possibly prevent shock from occurring due to the donor plasma which is foreign to the patient's body.

In furtherance of the problems associated with the use of donor plasma is the fact that there is a limited supply and that supply can be cut short by reason of contamination, other emergencies, or simply that a particular patient needs a rare type of plasma.

The problems described are those which plague the use of extracorporeal circuits and the associated reuse of blood. While steps have been made toward effectively and simply resolving these problems, no satisfactory solution has heretofore been provided. My method and apparatus is specifically designed to overcome the aforementioned problems. It is, therefore, to the effective resolution of these problems that the present invention is directed.

SUMMARY OF THE INVENTION

The principle object of the present invention is to provide a simple and reliable method which overcomes the difficulties previously mentioned by reclaiming virtually all of a patient's whole blood and plasma contaminated by heparin during cardiopulmonary bypass surgery for immediate reintroduction into the patient. In particular, the present invention relates to a method of effectively neutralizing the heparin in collected extracorporeal circuit blood.

Applicant's invention makes use of the patient's whole blood, or separated plasma, in the extracorporeal circuit whereby approximately 2.5 liters of heparinized whole blood typically remains after surgery. Utilizing high capacity blood bags of a commercially available modified type with a novel use of multiple ports and a means for infusing a calculable amount of protamine sulfate or protamine (a heparin neutralization drug) into the blood bag, all heparin is effectively neutralized. By use of a multiple port bag the un-heparinized blood is available for infusion directly back into the patient without further treatment.

Accordingly, it is an object of the present invention to provide a means for the neutralization of heparin, or heparin-like chemicals, derivatives, or the like, infused into whole blood, or suspended in separated plasma, as anti-coagulants and providing a means allowing for the immediate reuse into a patient.

Yet another object of the present invention is the use of a method for calculating an amount of protamine, or the like, to be mixed into a volume of blood containing other anti-coagulants such as Citrate Phosphate Dextrose Adenine Solution (CPDA) or the like.

Still another object of the present invention is to avoid shearing of blood cells by minimizing blood transferring, centrifugation, or other processing means.

Yet still another object of the present invention is to use modified commercially available blood bags having a novel use of multiple ports allowing for the collection of heparinized blood through a first inlet port, injection of protamine into the blood through a second inlet port, and infusing the non-heparin blood into a patient through a discharge port.

Yet another object of the present invention is to provide a method of reusing blood that is portable, utilizes existing equipment found in a conventional hospital, is easily understood, and inexpensive to incorporate.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

As required, detailed embodiments of the present invention are disclosed herein. However, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Figure 1:
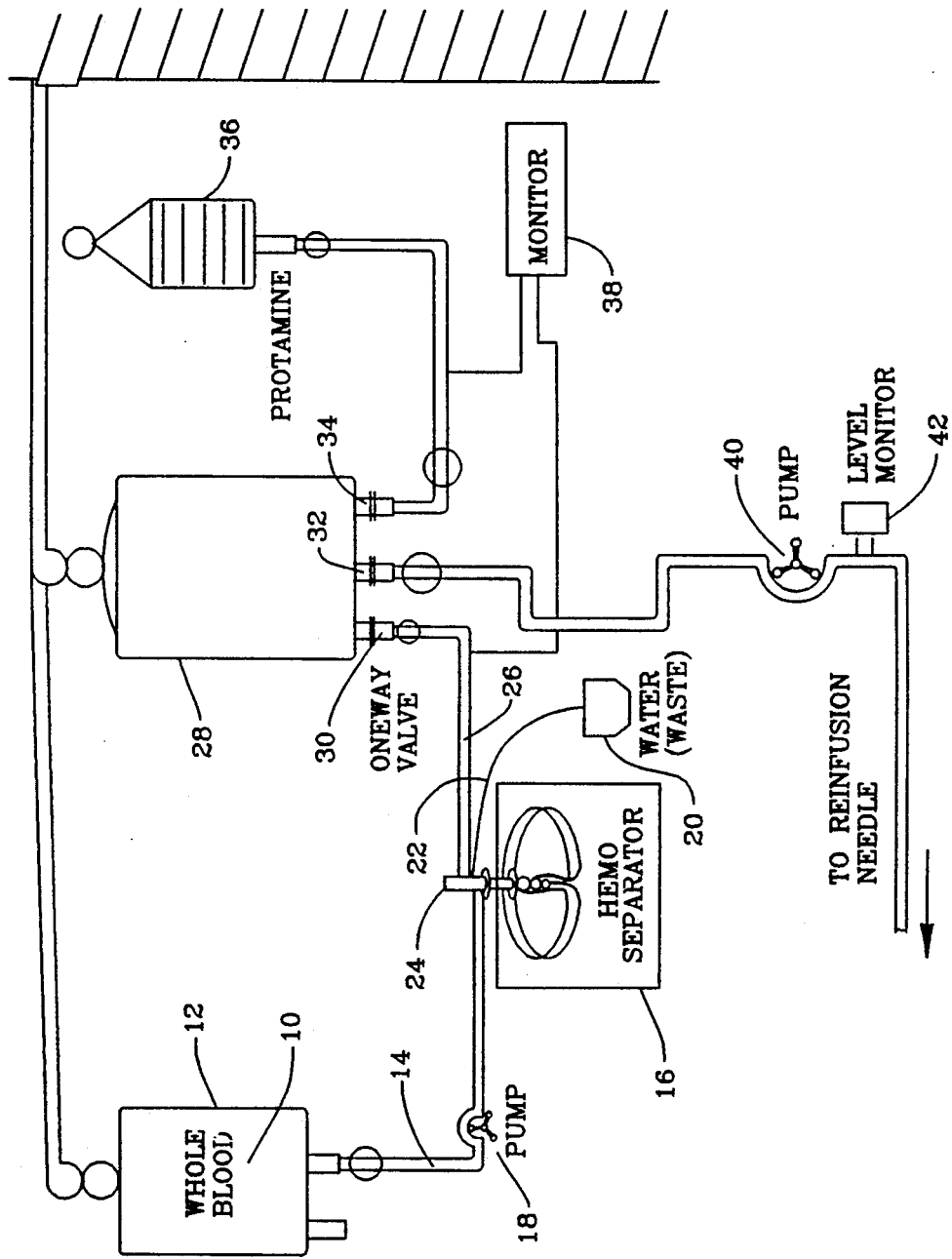
FIG. 1 is a schematic representation of the whole blood collection system of the present invention.

Referring to the drawings in more detail, FIG. 1 is a schematic representation of the whole blood collection system of the present invention. Upon disconnecting the extracorporeal circuit from the patient of which approximately 2.5 liters of the heparinized whole blood remains, whole blood 10 containing the heparin as well as primer water and CPDA is held in an interim collection container 12, or the extracorporeal circuit itself. The collection container is deemed to represent any device (eg. perfusion) in which the patient's whole blood remains after disconnecting the patient from the extracorporeal circuit. Inflow conduit 14 (arterial) of a hemo-concentrator 16 is connected to a purge port, or any other designated site, on the collection container. Arterial pump 18 is set to approximately 100-150 cc/min for directing the blood 10 through the hemo-concentrator 16 wherein the whole blood is separated from the primer water and the primer water 20 discarded. The water discharge port 22 of hemo-concentrator 16 is connected to a vacuum 24 having a draw of approximately 250-500 mm/hg. While a single pass of extra corporeal circuit blood through a hemo-concentrator removes over 80% of the primer water, multiple passes may be used for further concentrating. A chase fluid may also be used to purge the extracorporeal circuit and the blood collection system for optimum blood recovery, the amount of chase fluid being the prime volume of each component added together.

Outflow conduit 26 (venous) of the hemo-concentrator 16 is coupled to a modified collection bag 28 having a plurality of ports with a best mode envisioned having three ports. A first inlet port 30 for blood infusion, a second inlet, or discharge, port 32 having a pierceable resealing membrane for maintaining of sterility and for blood transfusion into the patient, and a third port 34 for injection of a heparin neutralization chemical such as pretamine from vessel 36, as well as for blood sampling. It has been found that the use of a resealable membrane for port 34 ensures sterility of the process. Collection bag 28 requires a capacity between 500 & 900 ml because it holds all of the extracorporeal fluid, CPDA and the heparin neutralizing agent. The purpose of bag 28 is to facilitate the collection of all whole blood as mixed with heparin, CPDA, less the primer water in a single collection bag whose volume, due to the unique capture of all fluids in a single bag and the need for later chemical addition, is of a suitable size.

Protamine 36, or the like, is then added to the collection bag 28 through the injection port 34 in accordance with the following formulation:

$$\text{Protamine} = \frac{\text{mg Hep.}}{\text{Kg Wt.}} \times \frac{\text{mg Prot.}}{\text{mg Hep.}} \times \frac{\text{Kg Wt.}}{\text{ml Bld}} \times \text{ml Bld}$$

where: Hep. = Heparin
Prot. = Protamine
Bld = Blood

For every 450 ml of whole blood retrieved it is found that 37 mg of Protamine must be added.

EXAMPLE I

Based on:
3 mg Hep/Kg of body weight;
1.5 mg Prot/1 mg Hep;
55 cc blood volume/1 Kg body weight.

$$\frac{3 \text{ mg Hep.}}{1 \text{ Kg Wt.}} \times \frac{1.5 \text{ mg Prot.}}{1.0 \text{ mg Hep}} \times \frac{1 \text{ Kg Wt.}}{55 \text{ ml Blood}} \times 450 \text{ ml Bld}$$

Thus, for total heparin reduction based upon the data provided, 37 mg of Protamine is needed. Protamine addition must be between the range of 1.2 mg and 1.9 mg for effective neutralization. The optimum amount of 1.5 mg is presented as the best mode at time of application.

The amount of heparin neutralizing agent required can also be calculated by use of a conventional monitoring system 38 capable of detecting the level of heparin in a blood stream. By use of such a monitor, in combination with a means for automatically calculating the amount of heparin neutralizing agent needed according to my formula, the monitor can be set up to automatically induce the heparin neutralizing agent by use of a solenoid valve, not shown, energized to release a set volume in accordance with the monitor's instructions.

The whole blood can now be injected into a patient by reinfusion from port 32 by gravity, I-V trickling, pressure from pump 40, and so forth. A monitor 42 may further be installed as a fail safe.

Figure 2:
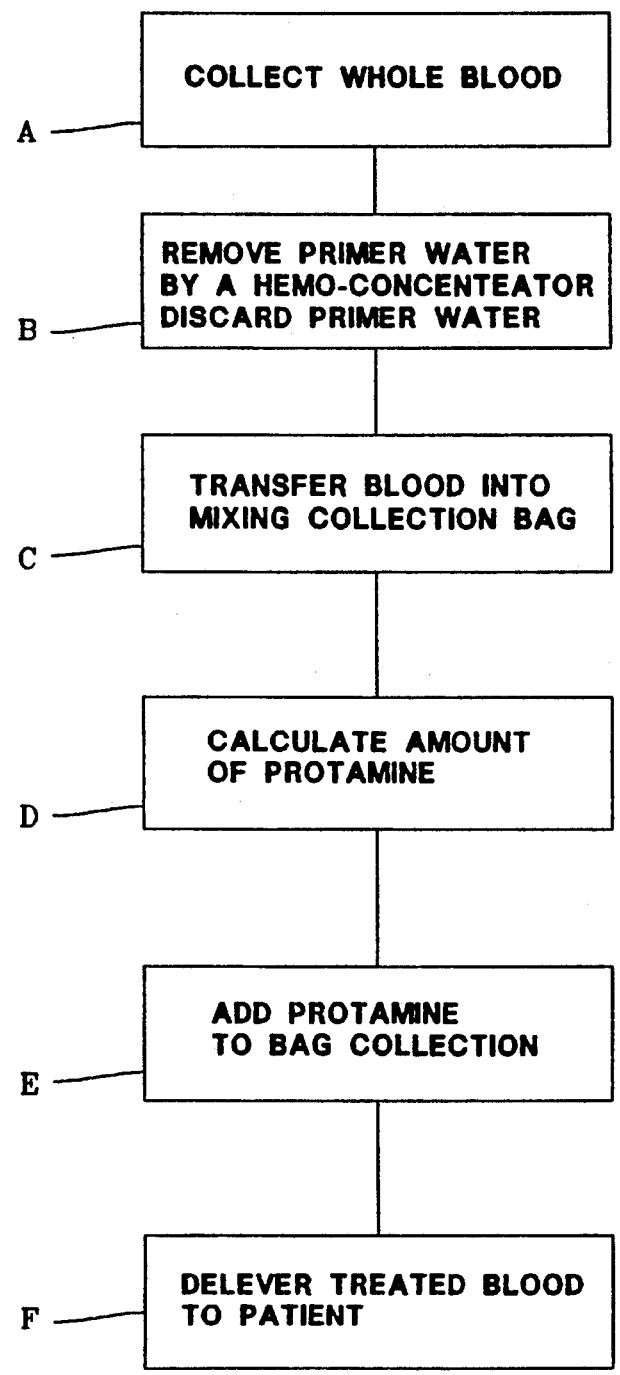
FIG. 2 is a flow chart of the steps for treating extracorporeal circuit blood for heparin neutralization and subsequent infusion into a patient.

Referring now to FIG. 2, the method of the instant invention is shown according to the steps of:

(a) collecting blood containing heparin from the extracorporeal circuit;

(b) optionally removing primer water from the blood by hemo-concentrating or the like and discarding the primer water;

(c) transferring the blood into a mixing container containing CPDA or the like;

(d) calculating a specified amount of heparin neutralizing chemical required such as Protamine, as a function of the amount of collected blood and the CPDA contained in said mixing container;

(e) transferring said specified amount of said neutralizing chemical into said container;

(f) infusing the contents of said container into the patient.

It is to be understood that while I have illustrated and described certain examples of practicing my method for neutralizing heparin, it is not to be limited to the specific examples of components utilized in accomplishing the method herein describe and shown. It will be apparent

What I claim as new and desire to secure by letters patent of the United States is:

1. A method of recovering deheparinized whole blood from an extracorporeal circuit for infusion into a patient, comprising the steps of:
   (a) collecting whole blood having heparin;
   (b) transferring the blood into a mixing container and mixing the blood with an anti-coagulant other than heparin;
   (c) transferring a heparin neutralizing agent calculated as a function of the quantity of transferred blood and the anti-coagulants present in the blood of the extracorporeal circuit into said container;
   (d) infusing the contents of said container into the patient.

2. The method according to claim 1 wherein said anti-coagulant other than heparin is CPDA.

3. The method according to claim 1 wherein the neutralizing chemical of step (c) is protamine.

4. The method according to claim 1 wherein the container of step (b) is a blood bag having a volume between 600 and 800 ml.

5. The method according to claim 4 wherein said blood bag has a plurality of ports.

6. The method according to claim 5 wherein said ports are further defined as a blood infusion port, a blood transfusion port, and a drug injection port.

7. The method according to claim 6 wherein said neutralizing chemical is infused through said drug infusion port.

8. The method according to claim 1 wherein the predetermined amount of heparin neutralizing agent is calculated according to the following equation:

$$\text{Protamine} = \frac{\text{mg Hep.}}{\text{kg Wt.}} \times \frac{\text{mg Prot.}}{\text{mg Hep}} \times \frac{\text{kg Wt.}}{\text{ml Bld}} \times \text{ml Bld}$$

wherein "Kg wt." refers to the weight in kg of the patient.

9. The method according to claim 8 wherein mg Prot. is between 1.2 and 1.9 mg Protamine.

10. The method according to claim 9 wherein mg Prot. is 1.5 mg Protamine.

11. A method of recovering deheparinized whole blood from an extracorporeal circuit for infusion into a patient comprising the steps of:
   (a) collecting whole blood having heparin from said circuit;
   (b) removing primer water from the blood by hemo-concentrating and discarding the primer water;
   (c) transferring the blood into a mixing container;
   (d) mixing an anti-coagulant other than heparin with said blood;
   (e) calculating an amount of heparin neutralizing chemical in relation to the amount of said transferred blood and the amount of heparin in the transferred blood or the contents of the container;
   (f) transferring said amount of said neutralizing chemical into said container;
   (g) infusing the de-heparinized blood into the patient.

12. A method of recovering de-heparinized plasma comprising the steps of:
   (a) collecting plasma having heparin:
   (b) removing primer water from the plasma by hemo-concentrating and discarding the primer water;
   (c) transferring the plasma into a mixing container having an anti-coagulant;
   (d) calculating an amount of heparin neutralizing chemical in relation to transferred plasma and said anti-coagulant;
   (e) transferring an amount of said neutralizing chemical into said container;
   (f) infusing the contents of said container into a patient.

13. The method according to claim 12 wherein said heparin neutralizing chemical of step (d) is protamine.

14. The method according to claim 12 wherein said anti-coagulant of step (c) is CPDA.

15. The method according to claim 12 wherein said neutralizing chemical of step (e) is infused through said drug infusion port.

16. The method according to claim 12 wherein step (e) further comprises the step of inverting said container.

17. The method according to claim 11 wherein the container of step (c) is further defined as a blood bag having a volume between 600 and 800 ml.

18. The method according to claim 17 wherein said blood bag defines a plurality of ports further defined as a blood infusion port, a blood transfusion port, and a drug injection port.

19. A method of recovering whole blood having CPDA anti-coagulant comprising the steps of:

20. A method for maintaining blood in an anti-coagulated state, comprising the steps of:
   (a) providing a quantity of extracorporeal blood containing a first anti-coagulant;
   (b) when desired to re-infuse a patient with said blood, doubly anti-coagulating said blood by mixing said anti-coagulated blood with a second anti-coagulant other than heparin;
   (c) mixing said doubly anti-coagulated blood with a heparin neutralizing agent.

21. The method of claim 20, further comprising the step of re-infusing said patient with said deheparinized whole blood in an anti-coagulated state.

22. The method of claim 20, wherein said first anti-coagulant is heparin.

23. The method of claim 20, wherein said second anti-coagulant is CPDA.

24. The method of claim 20, wherein said heparin neutralizing agent is protamine.

* * * * *